(12) United States Patent
Heck et al.

(10) Patent No.: US 8,100,982 B2
(45) Date of Patent: *Jan. 24, 2012

(54) MODULAR DIAPHYSEAL AND COLLAR IMPLANT

(75) Inventors: Robert K. Heck, Memphis, TN (US); Stephen A. Hazebrouck, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 1497 days.

This patent is subject to a terminal disclaimer.

(21) Appl. No.: 11/302,804

(22) Filed: Dec. 14, 2005

(65) Prior Publication Data

US 2006/0167555 A1    Jul. 27, 2006

Related U.S. Application Data

(60) Provisional application No. 60/637,015, filed on Dec. 17, 2004, provisional application No. 60/731,999, filed on Oct. 31, 2005, provisional application No. 60/732,402, filed on Oct. 31, 2005.

(51) Int. Cl.
    *A61F 2/38*    (2006.01)
(52) U.S. Cl. ................................. 623/20.35
(58) Field of Classification Search .... 623/19.11–19.14, 623/20.35–20.36, 22.4–23.39
    See application file for complete search history.

(56) References Cited

U.S. PATENT DOCUMENTS

| | | | |
|---|---|---|---|
| 3,605,123 A | 9/1971 | Hahn | |
| 3,848,272 A | 11/1974 | Noiles | |
| 4,219,893 A | 9/1980 | Noiles | |
| 4,301,553 A | 11/1981 | Noiles | |
| 4,384,373 A | 5/1983 | Sivash | |
| 4,502,160 A | 3/1985 | Moore et al. | |
| 4,676,797 A | 6/1987 | Anapliotis et al. | |
| 4,695,283 A | 9/1987 | Aldinger | |
| 4,787,907 A | 11/1988 | Carignan | |
| 4,790,852 A | 12/1988 | Noiles | |
| 4,822,366 A | 4/1989 | Bolesky | |
| 4,846,839 A | 7/1989 | Noiles | |
| 4,938,768 A | 7/1990 | Wu | |

(Continued)

FOREIGN PATENT DOCUMENTS

WO    WO 02/47585 A1    6/2002

OTHER PUBLICATIONS

Biomet, Orthopaedic Salvage System Overview.

(Continued)

*Primary Examiner* — David Isabella
*Assistant Examiner* — Ann Schillinger

(57) ABSTRACT

A modular implant system includes a set of anatomically-designed diaphyseal fitting and filling modular implant components and collars. The diaphyseal component connects with a selected intramedullary stem and with a selected collar component. The collar component connects to another implant component such as a modular articular component, a segmental component or an intercalary component. The diaphyseal component has a tapered porous surface that is received with a tapered bore in the bone diaphysis that is prepared to match the size and shape of the tapered porous surface. The collar component has a porous surface for tissue ingrowth, such as the periosteum, to seal the intramedullary canal. The diaphyseal implant is easy to insert and remove, does not bind before fully seating to prevent stress shielding, and eliminates the long lever arm created when fixation occurs only at the tip of the stem, and should eliminate related stem loosening.

22 Claims, 13 Drawing Sheets

U.S. PATENT DOCUMENTS

| | | | |
|---|---|---|---|
| 5,032,130 | A | 7/1991 | Schelhas et al. |
| 5,080,685 | A | 1/1992 | Bolesky et al. |
| 5,152,796 | A | 10/1992 | Slamin |
| 5,181,928 | A | 1/1993 | Bolesky et al. |
| 5,286,260 | A | 2/1994 | Bolesky et al. |
| 5,330,534 | A | 7/1994 | Herrington et al. |
| 5,358,524 | A | 10/1994 | Richelsoph |
| 5,370,706 | A | 12/1994 | Bolesky et al. |
| 5,653,765 | A | 8/1997 | McTighe et al. |
| 5,658,349 | A | 8/1997 | Brooks et al. |
| 5,755,805 | A | 5/1998 | Whiteside |
| 5,782,921 | A | 7/1998 | Colleran et al. |
| 5,824,097 | A | 10/1998 | Gabriel et al. |
| 5,876,459 | A | 3/1999 | Powell |
| 5,906,644 | A | 5/1999 | Powell |
| 6,063,122 | A | 5/2000 | O'Neil et al. |
| 6,071,311 | A | 6/2000 | O'Neil et al. |
| 6,102,956 | A * | 8/2000 | Kranz ............. 623/23.15 |
| 6,139,584 | A | 10/2000 | Ochoa et al. |
| 6,171,342 | B1 | 1/2001 | O'Neil |
| 6,214,052 | B1 | 4/2001 | Burkinshaw |
| 6,264,699 | B1 | 7/2001 | Noiles et al. |
| 6,428,578 | B2 | 8/2002 | White |
| 6,527,807 | B1 | 3/2003 | O'Neil et al. |
| 6,613,092 | B1 * | 9/2003 | Kana et al. ............. 623/20.15 |
| 6,692,530 | B2 | 2/2004 | Doubler et al. |
| 6,712,858 | B1 | 3/2004 | Grundei et al. |
| 6,723,129 | B2 | 4/2004 | Dwyer et al. |
| 6,755,862 | B2 | 6/2004 | Keynan |
| 6,786,931 | B2 | 9/2004 | Hazebrouck |
| 6,824,566 | B2 | 11/2004 | Kana et al. |
| 6,866,683 | B2 | 3/2005 | Gerbec et al. |
| 6,875,239 | B2 | 4/2005 | Gerbec et al. |
| 6,902,583 | B2 | 6/2005 | Gerbec et al. |
| 7,175,664 | B1 | 2/2007 | Lakin et al. |
| 7,507,256 | B2 * | 3/2009 | Heck et al. ............. 623/20.15 |
| 2003/0204267 | A1 | 10/2003 | Hazebrouck |
| 2004/0049285 | A1 | 3/2004 | Haas |
| 2004/0162621 | A1 | 8/2004 | Crofford |
| 2004/0193267 | A1 | 9/2004 | Jones |
| 2004/0193268 | A1 | 9/2004 | Hazebrouck |
| 2005/0071014 | A1 | 3/2005 | Barnett et al. |
| 2005/0107794 | A1 | 5/2005 | Hazebrouck |
| 2005/0107883 | A1 | 5/2005 | Goodfried |
| 2005/0154470 | A1 | 7/2005 | Sekel |
| 2006/0030945 | A1 * | 2/2006 | Wright ............. 623/20.15 |
| 2006/0041317 | A1 | 2/2006 | Hazebrouck |
| 2006/0167560 | A1 | 7/2006 | Heck et al. |

OTHER PUBLICATIONS

De Puy, Reconstructive/Revision Products, pp. 182 & 184.
DePuy Orthopaedics, Inc., M.B.T. Revision Tray, 2004, DePuy Orthopaedics, Inc., Warsaw, Indiana.
DePuy Orthopaedics, Inc., S-ROM NOILES Rotating Hinge, 2002, DePuy Orthopaedics, Inc., Warsaw, Indiana.
International Search Report dated May 11, 2006, for corresponding PCT Application PCT/US05/45197.
Non-Final Rejection—Oct. 11, 2007—US Pat. 7,507,256.
Final Rejection—Jul. 14, 2008—US Pat. 7,507,256.
Notice of Allowance—Nov. 18, 2008—US Pat 7,507,256.
Restriction/Election Requirement—Apr. 14, 2009—U.S. Appl. No. 11/302,571.
Non-Final Rejection—Aug. 4, 2009—U.S. Appl. No. 11/302,571.
Japanese Search Report for Corresponding Patent Application No. 2007-546849, Dated Apr. 27, 2010, 4 Pages.
Japanese Search Report for Corresponding Patent Application No. 2007-546850, Dated Apr. 27, 2010, 2 Pages.
Japanese Search Report for Corresponding Patent Application No. 2007-546814, Dated Apr. 27, 2010, 2 Pages.
Australian Search Report in App. No. 2005317184, Dated Jul. 22, 2010, 3 Pages.
Australian Search Report in App. No. 2005316640, Dated Aug. 16, 2010, 3 Pages.

* cited by examiner

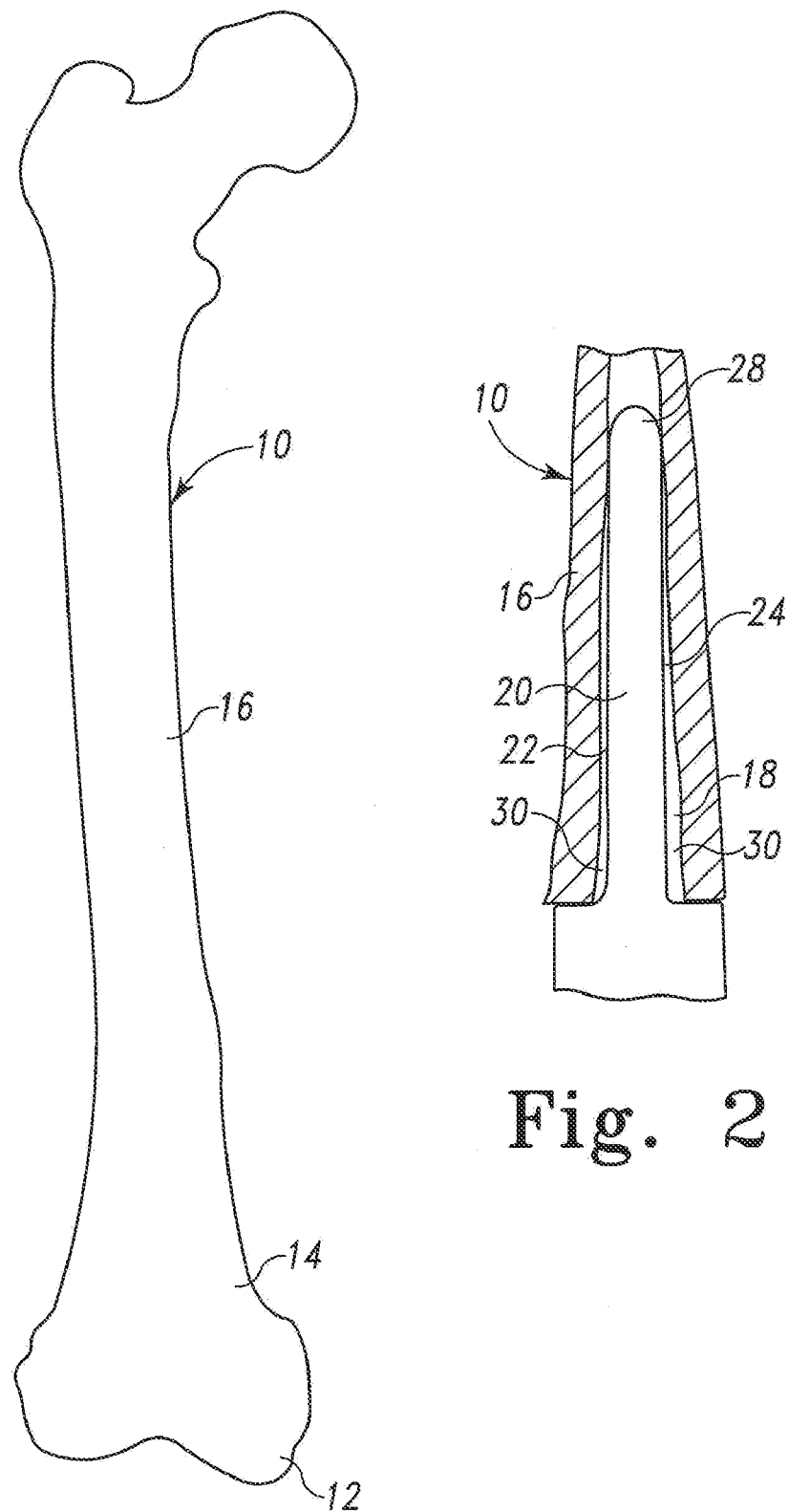

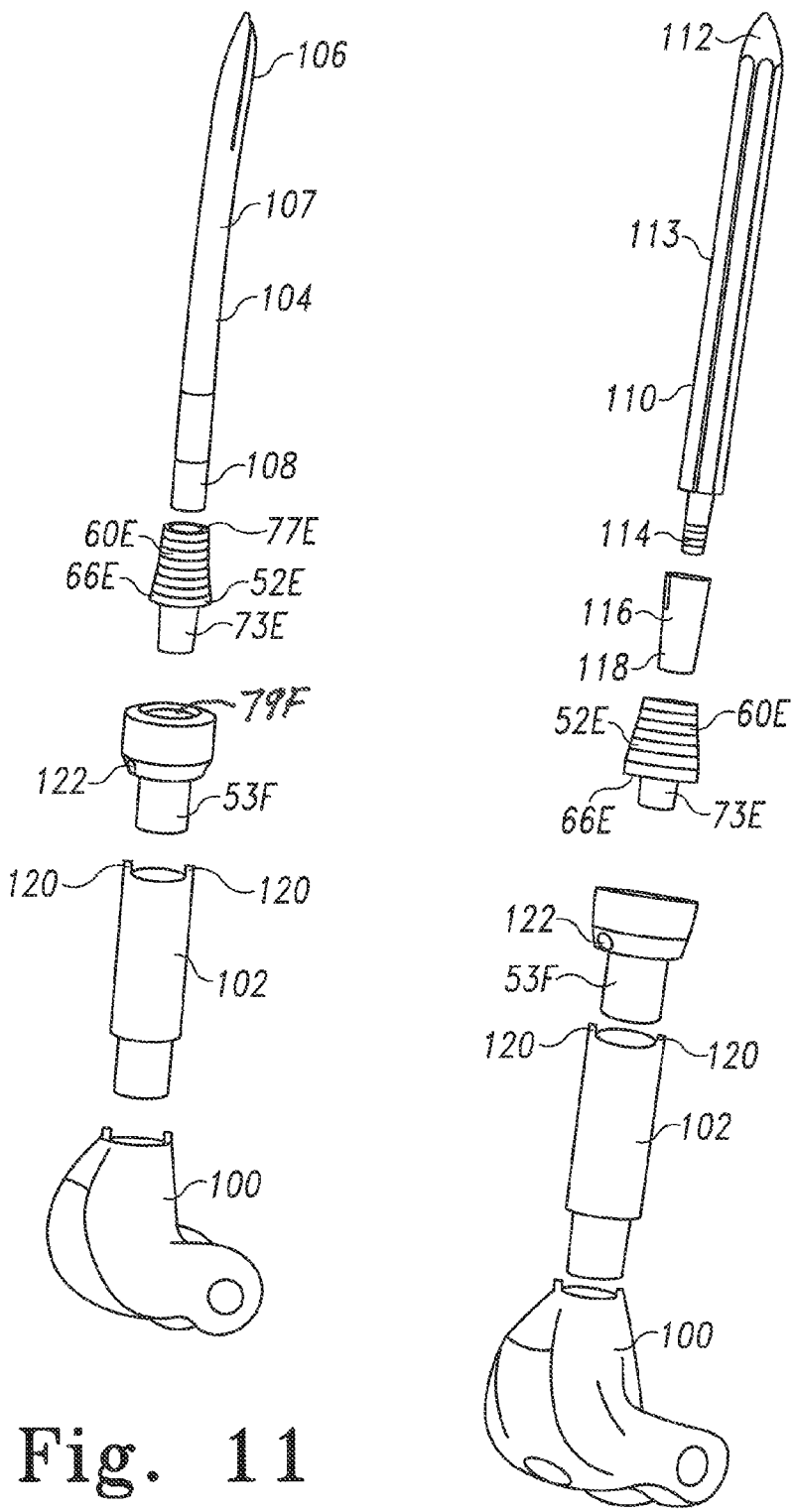

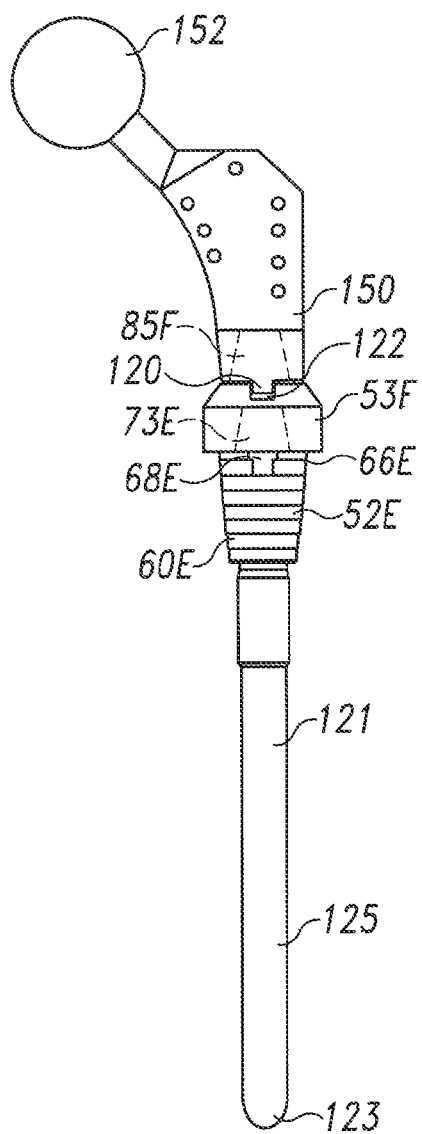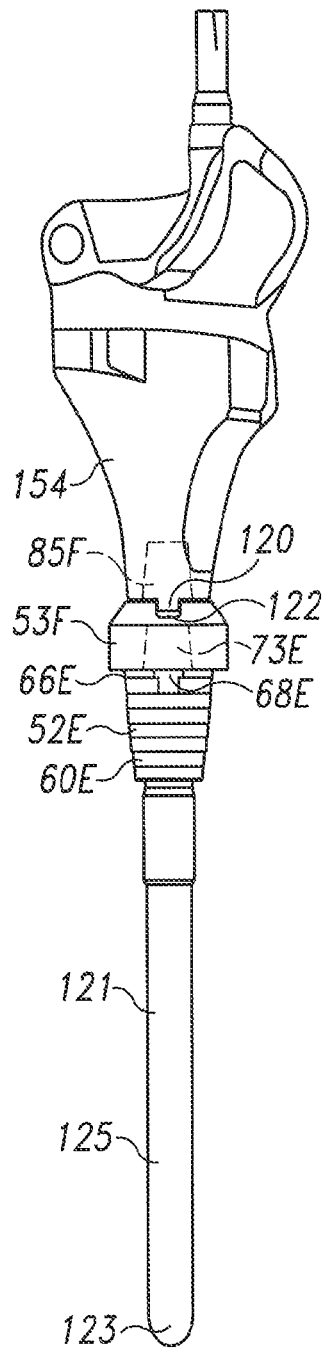
Fig. 17
Fig. 18

MODULAR DIAPHYSEAL AND COLLAR IMPLANT

CROSS-REFERENCE TO RELATED APPLICATIONS

The present invention claims priority to U.S. Provisional Patent Application Ser. No. 60/637,015, filed on Dec. 17, 2004 by Robert K. Heck and Stephen A. Hazebrouck and entitled "Modular Implant System and Method with Diaphyseal Implant," U.S. Provisional Patent Application Ser. No. 60/731,999, filed on Oct. 31, 2005 by Robert K. Heck and Stephen A. Hazebrouck, and entitled "Modular Diaphyseal and Collar Implant," and U.S. Provisional Patent Application Ser. No. 60/732,402, filed on Oct. 31, 2005 by Robert K. Heck and Stephen A. Hazebrouck and entitled "Modular Implant System and Method with Diaphyseal Implant and Adapter," all of which are incorporated by reference herein in their entireties.

BACKGROUND OF THE INVENTION

The present invention relates generally to prosthetic joints and, more particularly, to modular orthopaedic lower extremity implant systems.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The distal femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

The hip joint consists of the bone interface of the proximal end of the femur and the acetabulum of the hipbone. The proximal femur is configured with a ball-shaped head, which is received within and articulates against the cup-shaped cavity defined by the acetabulum.

When the knee or hip joint is damaged whether as a result of an accident or illness, a prosthetic replacement of the damaged joint may be necessary to relieve pain and to restore normal use to the joint. Typically the entire joint is replaced by means of a surgical procedure, which involves removal of the surfaces of the corresponding damaged bones and replacement of these surfaces with prosthetic implants. This replacement of a native joint of the leg with a prosthetic joint is referred to as primary total-knee arthroplasty and primary total-hip arthroplasty.

On occasion, the primary prosthesis fails. Failure can result from many causes, including wear, aseptic loosening, osteolysis, ligamentous instability, arthrofibrosis and patellofemoral complications. When the failure is debilitating, revision surgery may be necessary. In a revision, the primary prosthesis is removed and replaced with components of a revision prosthetic system.

Implant systems for both primary and revision applications are available from a variety of manufacturers, including DePuy Orthopaedics, Inc. of Warsaw, Ind. DePuy and others offer several different systems for both primary and revision applications. For example, DePuy Orthopaedics offers the P.F.C. SIGMA® Knee System, the LCS® Total Knee System, and the S-ROM Modular Total Knee System. Each of these orthopaedic knee systems includes several components, some appropriate for use in primary knee arthroplasty and some appropriate for use in revision surgery.

DePuy Orthopaedics also offers other orthopaedic implant systems for other applications. One such system is the LPS System. The LPS System is provided for use in cases of neoplastic diseases (e.g., osteosarcomas, chrondrosarcomas, giant cell tumors, bone tumors) requiring extensive resections and replacements of the proximal and/or distal femur, severe trauma, disease (e.g., avascular necrosis, osteoarthritis and inflammatory joint disease requiring extensive resection and replacement of the proximal and/or distal femur), and resection cases requiring extensive resection and replacement of the proximal, distal or total femur or proximal tibia (e.g., end-stage revision). Any of these conditions or a combination thereof can lead to significant amounts of bone loss. The LPS System provides components that can replace all or significant portions of a particular bone, such as the femur or tibia. The DePuy LPS System is described more fully in U.S. patent application Ser. No. 10/135,791, entitled "Modular Limb Preservation System", filed Apr. 30, 2002 by Hazebrouck et al., U.S. Pat. Publication No. US2003/0204267A1 (published Oct. 30, 2003) which is incorporated by reference herein in its entirety. Other companies also offer systems for similar indications.

The LPS system provides a comprehensive set of modular implants capable of addressing a wide range of orthopaedic conditions. Components of the LPS system can be combined in a variety of ways to account for variations in patient anatomy and differences in the amount of native bone remaining. As disclosed in U.S. Pat. Publication No. US2003/0204267A1, the modular components can be combined to replace the proximal or distal femur, total femur, proximal tibia or the mid-shaft of a long bone. Similar systems can be used with other long bones, such as the bones of the upper arm.

Many of the combinations of components possible with the LPS system include stem components that are configured for implantation within the intramedullary canal of the remaining bone. Metaphyseal sleeves are available for use in the LPS system, as disclosed, for example, in U.S. patent application Ser. No. 10/817,051, entitled "Modular Implant System with Fully Porous Coated Sleeve", filed on Apr. 2, 2004 by Goodfried, Hazebrouck, Lester and Brown (U.S. Pat. Publication No. 2005/0107883A1), which is incorporated by reference herein in its entirety. However, in some instances, the stem components must be used with implant components that have replaced the entire articulating portion of the bone and the metaphysis of the bone. In some indications, the remaining native bone comprises the diaphysis or shaft of the long bone, and a metaphyseal sleeve cannot be used.

An example of a long bone is illustrated in FIG. 1; in FIG. 1, the bone 10 is the femur. FIG. 2 illustrates the femur of FIG. 1 after the distal articulating end 12 and metaphysis 14 of the bone 10 have been removed due to neoplastic disease, trauma, disease or as part of an end-stage revision. The diaphysis of the bone is illustrated at 16 in FIGS. 1-2.

As shown in FIG. 2, the intramedullary canal 18 of the diaphysis 16 of the long bone 10 generally tapers, while the implant stem extensions 20 generally have parallel sides, such as those shown at 22, 24. As a result, the implant stem extension 20 frequently contacts the native bone tissue at the free end or tip 28 of the stem extension 20, while leaving gaps 30 along much of the length of the stem extension 20. Although these gaps 30 could be filled with bone cement, for optimal fixation it is desirable to use porous coated stem extensions. Such porous coated stem extensions tend to bind before becoming fully seated. Consequently, in cases where the stem extension is porous coated to encourage bone ingrowth, the bone ingrowth is frequently limited to the free end 28 of the stem. With bone ingrowth limited to the free end of the stem extension, there is stress shielding of the bone surrounding the remainder of the stem extension, and a long lever arm is created; both of these effects can lead to early loosening of the implant. Additionally, when significant ingrowth does occur and the stem extension must subsequently be removed, the procedure can be difficult.

SUMMARY OF THE INVENTION

The present invention addresses the need for an implant system that can be effectively used in the diaphyseal region of a long bone and for a surgical method for implanting a system in the diaphyseal region of a long bone.

In one aspect, the present invention addresses this need by providing a modular orthopaedic implant system comprising a diaphyseal component and a collar component. The diaphyseal component includes a first end, a second end and a tapered outer surface. The first end has a post and the second end has a bore co-axial with the post of the first end. A longitudinal axis extends from the first end to the second end. The longitudinal axis extends through the post at the first end and the bore at the second end. The tapered outer surface is between the first end and the second end, and has a maximum outer diameter at the first end and a minimum outer diameter at the second end. At least part of the tapered outer surface is porous. The collar component includes a first end, a second end and a substantially cylindrical portion between the first end and the second end. The first end of the collar component has a post, and the second end has a bore co-axial with the post of the first end. A longitudinal axis extends from the first end to the second end; the longitudinal axis extends through the post at the first end and the bore at the second end. The substantially cylindrical portion surrounds at least a portion of the bore at the second end and includes an annular surface disposed perpendicular to the longitudinal axis of the collar component at the second end of the collar component. The annular surface has a maximum outer diameter. The post of the diaphyseal component and the bore of the collar component are sized and shaped so that the diaphyseal component and the collar component can be assembled and locked together by inserting the post of the diaphyseal component into the bore of the collar component.

In another aspect, the present invention addresses this need by providing an orthopaedic implant system for replacing a portion of a long bone. The long bone has an articulation portion, a diaphysis and an intramedullary canal. The kit includes a plurality of articulation components, a plurality of modular stems, a plurality of modular diaphyseal implant components, and a plurality of collar components. Each articulation component is shaped and sized to replace the articulation portion of the long bone, and includes a tapered bore having a first size. The modular stems are to be received in the intramedullary canal of the long bone. Each stem has a free end and an opposite end capable of being connected to another implant component. The modular diaphyseal implant components are capable of being connected to the modular stems. Each diaphyseal implant component includes a first end, a second end and a tapered outer surface. The first end has a tapered post and the second end is provided for connection to a selected modular stem. A longitudinal axis extends between the first end and the second end of each diaphyseal implant component. The tapered outer surface of each diaphyseal implant component has a minimum outer dimension at the second end and a maximum outer dimension positioned between the first end and the second end. Each collar component includes a first end having a post and a second end having a tapered bore co-axial with the post of the first end. The tapered bore of the collar component is smaller than the tapered bore of the articulation component. Each collar has a longitudinal axis extending from the first end to the second end. The longitudinal axis extends through the post at the first end and the bore on the second end. Each collar also has a substantially cylindrical portion between the first end and the second end. The substantially cylindrical portion surrounds at least a portion of the bore at the second end and includes an annular surface disposed transverse to the longitudinal axis of the diaphyseal implant component. The tapered post of each collar component is sized and shaped so that the each collar component can be assembled with each articulation component and frictionally locked together by inserting the tapered post of the collar into the tapered bore of the articulation component. The tapered post of each diaphyseal component is sized and shaped so that each diaphyseal component can be assembled with each collar component and frictionally locked together by inserting the tapered post of the diaphyseal component into the tapered bore of the collar component.

In another aspect, the present invention provides a method of replacing a portion of a long bone having an articulating surface, an intramedullary canal, a diaphysis spaced from the articulating surface, and a periosteum. A plurality of bone replacement components are provided; each bone replacement component is shaped and sized to replace a portion of the long bone, and each bone replacement component includes a tapered bore. A plurality of modular stems are also provided. The stems are to be received in the intramedullary canal of the long bone, and each stem has a free end and an opposite end capable of being connected to another implant component. A plurality of modular diaphyseal implant components are also provided. Each diaphyseal implant component includes a first end with a tapered post and a second end for connection to a selected modular stem. Each diaphyseal implant component also has a longitudinal axis extending between the first end and the second end and a tapered outer surface. The tapered outer surface has a minimum outer dimension at the second end and a maximum outer dimension positioned between the first end and the second end. At least two of the diaphyseal components have different maximum outer diameters. A plurality of collar components is also provided. Each collar component includes a first end having a post and a second end. The second end has a tapered bore co-axial with the post of the first end. The tapered bore of the collar component is smaller than the tapered bore of the bone replacement implant components. Each collar also has a longitudinal axis extending from the first end to the second end. The longitudinal axis extends through the post at the first end and the bore on the second end. A substantially cylindrical porous portion surrounds at least a portion of the bore at the second end. The cylindrical porous portion is between the first end and the second end. At least two of the collar components have different maximum outer diameters. In the method, the bone is resected to remove a portion of the bone and leave at least a portion of the diaphysis of the bone. A tapered bore is prepared in the diaphysis of the bone. One stem component, one diaphyseal component, one collar component and one bone replacement component are selected. An implant assembly is made by connecting the selected stem component to the second end of the selected diaphyseal component, inserting the tapered post of the selected diaphyseal component into the tapered bore of the selected collar component, and inserting the tapered post of the selected collar component into the tapered bore of the selected bone replacement component. The implant assembly is then implanted so that the stem component is received in the intramedullary canal, a substantial part of the diaphyseal component is received in the tapered bore in the diaphysis of the bone and the collar component is exposed outside of the bone.

BRIEF DESCRIPTION OF THE DRAWINGS

FIG. 1 is an anterior view of a left femur;

FIG. 2 is a cross-section of a portion of the diaphysis of the femur of FIG. 1, shown with a stem extension received in the intramedullary canal of the femur;

FIG. 11 is an exploded perspective view of a distal femoral implant assembly illustrating use of one of the diaphyseal components and collar components of FIGS. 3-4 in use with one style of stem extension;

FIG. 12 is an exploded perspective view similar to FIG. 11, but illustrating use of one of the diaphyseal components and collar components of FIGS. 3-4 in use with a different style of stem extension;

FIG. 17 is a side view of a proximal femoral implant assembly including one of the diaphyseal components and collar components of FIGS. 3-4;

FIG. 18 is a perspective view of a proximal tibial implant assembly including one of the diaphyseal components and collar components of FIGS. 3-4;

DETAILED DESCRIPTION

A modular orthopaedic knee implant system incorporating the principles of the present invention is illustrated in the accompanying drawings. The illustrated modular orthopaedic knee implant system includes components of several existing orthopaedic knee implant systems, along with new components that provide the orthopaedic surgeon with greater flexibility in selecting the appropriate components to suit the needs of an individual patient. These patient needs can include factors such as individual anatomy and the condition of the native bone tissue.

Figure 3:
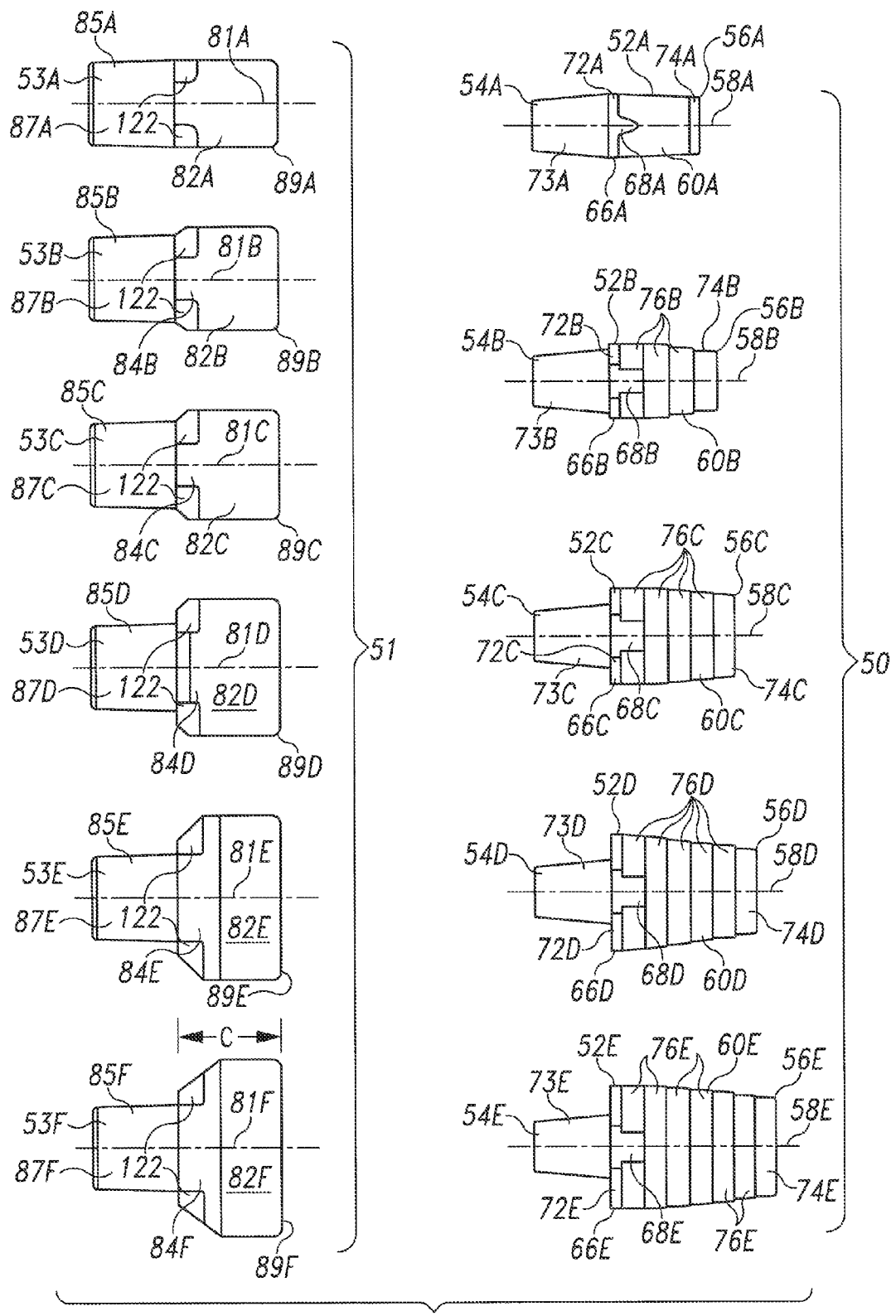
FIG. 3 is an elevation of an orthopaedic implant system illustrating the principles of the present invention, including a set of diaphyseal components and a set of collar components.

FIG. 3 illustrates a set 50 of diaphyseal components and a set of collar components 51 that may be used in the system or kit of the present invention. The illustrated set 50 of diaphyseal components includes five sizes of diaphyseal components, labeled 52A, 52B, 52C, 52D, 52E. The illustrated set of collar components 51 includes six sizes of collar components, labeled 53A, 53B, 53C, 53D, 53E, 53F.

The illustrated diaphyseal components 52A, 52B, 52C, 52D, 52E include several common features. The illustrated collar components 53A, 53B, 53C, 53D, 53E, 53F also include several common features. In the following description and in the drawings, like parts are identified with the same reference number, followed by a letter designation to identify the particular size of component.

Each of the illustrated diaphyseal components 52A, 52B, 52C, 52D, 52E has a first end 54A, 54B, 54C, 54D, 54E, a second end 56A, 56B, 56C, 56D, 56E and a longitudinal axis 58A, 58B, 58C, 58D, 58E extending from the first end 54A, 54B, 54C, 54D, 54E to the second end 56A, 56B, 56C, 56D, 56E. Each of the illustrated diaphyseal components 52A, 52B, 52C, 52D, 52E also has a tapered outer surface 60A, 60B, 60C, 60D, 60E.

The tapered outer surface 60A, 60B, 60C, 60D, 60E of each diaphyseal implant component 52A, 52B, 52C, 52D, 52E in the set 50 is of a different size to accommodate the needs of the individual patient's anatomy. The illustrated set includes sizes ranging from extra-extra-small 52A to large 52E.

The tapered outer surface 60A, 60B, 60C, 60D, 60E of each diaphyseal implant component 52A, 52B, 52C, 52D, 52E in the set 50 has a minimum outer diameter at the second end 56A, 56B, 56C, 56D, 56E and a maximum outer diameter spaced from the first end 54A, 54B, 54C, 54D, 54E and the second end 56A, 56B, 56C, 56D, 56E. The maximum outer diameter is indicated at 66A, 66B, 66C, 66D, 66E in FIGS. 3-6 and 9-20.

The tapered outer surface 60A, 60B, 60C, 60D, 60E, 60F may have a plurality of flats 68A, 68B, 68C, 68D, 68E at the maximum outer diameter 66A, 66B, 66C, 66D, 66E. The flats may be provided to help to limit rotation of the diaphyseal components 52A, 52B, 52C, 52D, 52E with respect to the bone after implantation, as described in more detail below. It should be understood that the diaphyseal implant components could be provided without such flats if desired.

Figure 5:
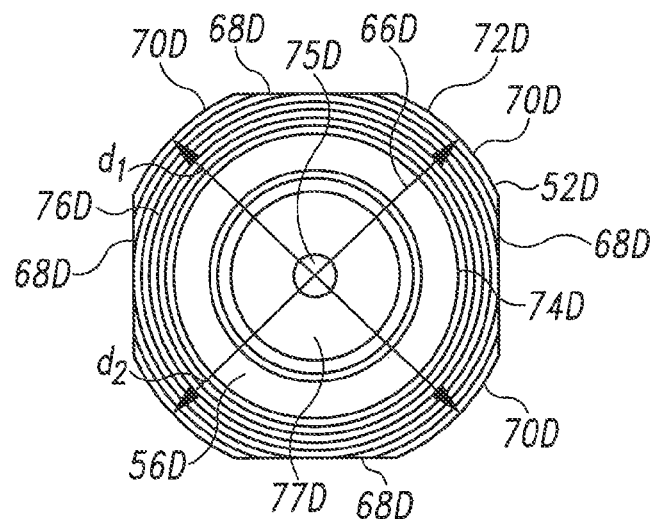
FIG. 5 is an end view of one of the diaphyseal components of FIGS. 3-4.
Figure 6:
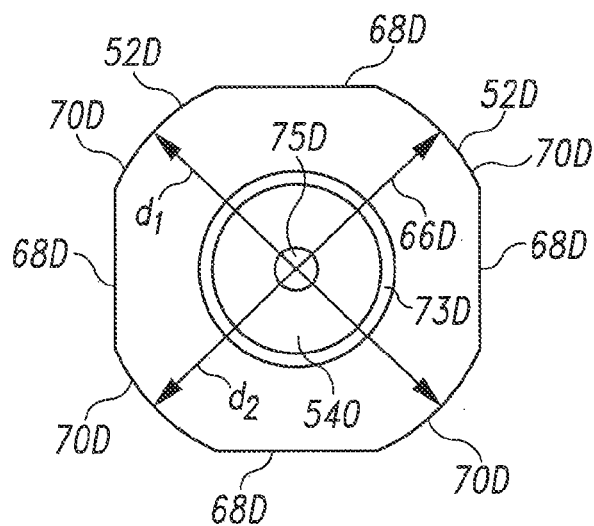
FIG. 6 is a view of the opposite end of the diaphyseal implant component of FIG. 5.

FIG. 5 illustrates an end view of one of the diaphyseal implant components 52D of the set 50, taken from the second end 56D of the component. FIG. 6 illustrates an end view of the same diaphyseal component 52D taken from the first end 54D of the component. As there shown, the tapered outer surface 60D has four equally spaced flats 68D connected by curved arcs 70D. The maximum transverse outer dimensions of the tapered outer surface 60D are shown at $d_1$ and $d_2$ in FIGS. 5-6; in the illustrated embodiments, $d_1=d_2$. Thus, the tapered outer surface 60D has the same maximum transverse outer dimension $d_1$, $d_2$ along two perpendicular axes at the maximum outer dimension 66D of the tapered outer surface 60D.

In the smallest size of diaphyseal implant component 52A most of the tapered outer surface 60A has a frustoconical shape, as shown in FIG. 3. Frusto-conical is intended to mean shaped like the frustum of a cone, that is, it has the shape of the basal part of a solid cone formed by cutting off the top by a plane parallel to the base. The smallest illustrated diaphyseal implant component 52A also has a first annular step 72A. In each of the other sizes of diaphyseal implant components 52B, 52C, 52D, 52E in the set 50, the tapered outer surface 60B, 60C, 60D, 60E comprises a plurality of annular steps: there is a first annular step 72B, 72C, 72D, 72E between the first end 54B, 54C, 54D, 54E and second end 56B, 56C, 56D, 56E of the diaphyseal components, a last annular step 74B, 74C, 74D, 74E at the second end 56B, 56C, 56D, 56E of the diaphyseal implant component and a plurality of intermediate annular steps 76B, 76C, 76D, 76E (shown in FIGS. 3, 9-10 and 13) between the first step 72B, 72C, 72D, 72E and last step 74B, 74C, 74D, 74E.

Each step has a substantially cylindrically shaped outer surface and a longitudinal height; the largest diameter steps deviate from a cylindrical shape in the illustrated embodiments because of the presence of the four flats 68.

In each illustrated size of diaphyseal implant component, the first annular step 72A, 72B, 72C, 72D, 72E has the greatest maximum transverse outer dimension, and the maximum transverse outer dimension of each step progressively decreases to the last annular step 74A, 74B, 74C, 74D, 74E which has the smallest maximum transverse outer dimension. In the illustrated set of diaphyseal implant components 52A, 52B, 52C, 52D, 52E examples of sizes and numbers of steps are provided in the following table:

| Extra Extra Small Diaphyseal Implant Component 52A | | | |
|---|---|---|---|
| | Height | Outer Diameter | Taper Angle |
| First step 72A | 2 mm | 12.95 mm | — |
| Frustoconical Portion 71A | 15.04 mm | 12.65 mm maximum to 10.67 mm minimum | 3° |
| Last Step 74A | 2 mm | 9.81 mm | |

| | Step Height | Step Outer Diameter | Overall Taper Angle |
|---|---|---|---|
| Extra Small Diaphyseal Implant Component 52B | | | |
| First step 72B | 2 mm | 15.23 mm | 4°52' |
| Second step | 4 mm | 14.37 mm | |
| Third step | 4 mm | 13.51 mm | |
| Fourth step | 4 mm | 12.65 mm | |
| Last step 74B | 4 mm | 11.79 mm | |
| Small Diaphyseal Implant Component 52C | | | |
| First step 72C | 2 mm | 19.09 mm | 4°33' |
| Second step | 4 mm | 18.37 mm | |
| Third step | 4 mm | 17.65 mm | |
| Fourth step | 4 mm | 16.93 mm | |
| Fifth step | 4 mm | 16.21 mm | |
| Last step 74C | 4 mm | 15.49 mm | |
| Medium Diaphyseal Implant Component 52D | | | |
| First step 72D | 2 mm | 22.53 mm | 6°35' |
| Second step | 4 mm | 21.51 mm | |
| Third step | 4 mm | 20.49 mm | |
| Fourth step | 4 mm | 19.47 mm | |
| Fifth step | 4 mm | 18.45 mm | |
| Sixth step | 4 mm | 17.43 mm | |
| Last step 74D | 4 mm | 16.41 mm | |
| Large Diaphyseal Implant Component 52E | | | |
| First step 72E | 2 mm | 26.51 mm | 6°39' |
| Second step | 4 mm | 25.49 mm | |
| Third step | 4 mm | 24.47 mm | |
| Fourth step | 4 mm | 23.45 mm | |
| Fifth step | 4 mm | 22.44 mm | |
| Sixth step | 4 mm | 21.42 mm | |
| Seventh step | 4 mm | 20.40 mm | |
| Last step 74E | 4 mm | 19.38 mm | |

In the above table, the Overall Taper Angle refers to the angle defined by a line tangent to the steps 72, 74, 76 and a line parallel to the longitudinal axis 58 in each size.

It should be understood that the sizes, numbers of steps and overall taper angles identified in the above tables are provided as examples only. The present invention is not limited to a stepped configuration or to any particular size, number of steps or overall angle of taper unless expressly called for in the claims. Moreover, although five sizes are illustrated in the set 50, fewer or more sizes could be provided; the invention is not limited to any number of sizes of implant components in a set unless expressly called for in the claims.

In each of the illustrated diaphyseal implant components 52A, 52B, 52C, 52D, 52E, most of the tapered outer surface is porous: the frusto-conical portion of the small implant component 52A and its first step 72A are porous and all of the first and intermediate steps 72B, 72C, 72D, 72E, 76B, 76C, 76D, 76E of the other sizes of diaphyseal implant components 52B, 52C, 52D, 52E are porous. The last or smallest diameter step 74 in each size is not porous in the illustrated embodiment.

As used herein, "porous" refers to a surface that is conducive to bone ingrowth for non-cemented fixation, and "smooth" refers to a surface that is not conducive to such bone ingrowth. Suitable porous surfaces can be made by many different methods: casting, embossing, etching, milling, machining, and coating such as by plasma-spraying or by bonding, for example. Bonded materials can comprise sintered metal beads, sintered metal mesh or screen, or sintered metal fibers, for example. Known, commercially available materials and techniques can be used to create the porous outer surfaces of the diaphyseal components and collar components: for example, POROCOAT® coating, used by DePuy Orthopaedics, Inc. of Warsaw, Ind., could be used, as well as other commercially available coatings. In addition, the porous surfaces may include other materials conducive to bone ingrowth, such as hydroxy apatite coatings, for example. It should be understood that the above-identified examples of materials, methods and commercial products are provided as examples only; the present invention is not limited to any particular material, method or commercial product for the porous surfaces unless expressly called for in the claims. In addition, it should be understood that as additional materials and methods become available to create surfaces that promote bony ingrowth, it is believed that such other materials and methods may also be useful with the present invention.

Each of the flats 68A, 68B, 68C, 68D, 68E in the illustrated diaphyseal components 52A, 52B, 52C, 52D, 52E is 6 mm high. The flats are disposed at 90° intervals around the first step and second step in the diaphyseal implant components 52B, 52C, 52D, 52E that have stepped tapered outer surfaces 60B, 60C, 60D, 60E and are also disposed at 90° intervals around the tapered frustoconical surface 71A and first step 72A of the smallest diaphyseal implant component 52A. It should be understood that the flats may have different dimensions and different positions.

Figure 4:
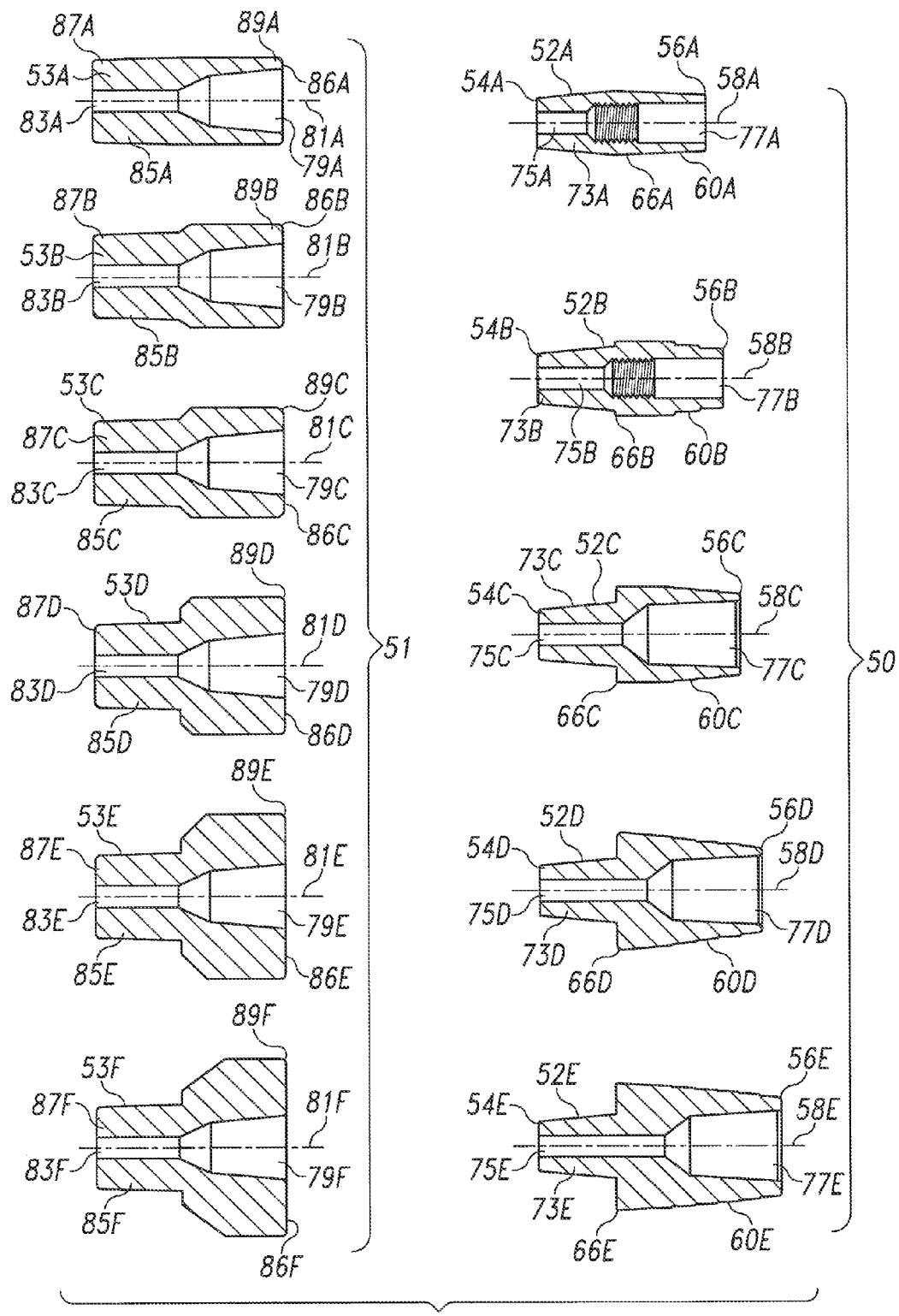
FIG. 4 is a longitudinal cross-section of the set of diaphyseal components and collar components of the system of FIG. 3.

As illustrated in FIGS. 3-4, each diaphyseal component 52A, 52B, 52C, 52D, 52E also includes a Morse taper post 73A, 73B, 73C, 73D, 73E at the first end 54A, 54B, 54C, 54D, 54E of the component. In the set of diaphyseal components, although the sizes of the tapered outer surfaces 60A, 60B, 60C, 60D, 60E vary, the Morse taper posts 73A, 73B, 73C, 73D, 73E of all of the diaphyseal components 52A, 52B, 52C, 52D, 52E are of the same size and shape. The Morse taper posts of the illustrated diaphyseal components are frusto-conical, with diameters of 12.87 mm (0.5069 inches) at the narrowest point, lengths of 15.25 mm (0.600 inches) and taper angles of 2°50'0". It should be understood that these and all dimensions provided in this description are provided for illustrative purposes only; the invention is not limited to these dimensions or any other dimension unless expressly called for in one of the claims.

As shown in FIG. 4, the Morse taper posts 73A, 73B, 73C, 73D, 73E all have longitudinal channels 75A, 75B, 75C, 75D, 75E aligned along their central longitudinal axes 58A, 58B, 58C, 58D, 58E that communicate with bores 77A, 77B, 77C, 77D, 77E at the second ends 56A, 56B, 56C, 56D, 56E of the diaphyseal components 52A, 52B, 52C, 52D, 52E. As described in more detail below, the bores 77A, 77B, 77C, 77D, 77E are provided for connecting stem members to the second ends of the diaphyseal components.

Figure 7:
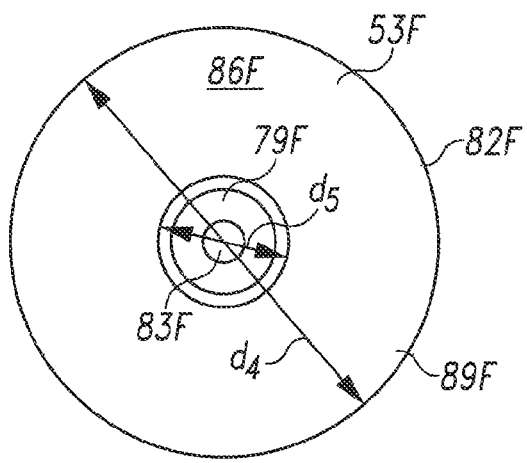
FIG. 7 is an end view of one of the collar components of FIGS. 3-4.

The Morse taper posts 73A, 73B79, 73C, 73D, 73E are sized and shaped to mate and frictionally lock with Morse taper bores A, 79B, 79C, 79D, 79E, 79F formed in the collar components 53A, 53B, 53C, 53D, 53E, 53F. All of the Morse taper bores 79A, 79B, 79C, 79D, 79E, 79F have the same size and shape. Accordingly, each collar component 53A, 53B, 53C, 53D, 53E, 53F is capable of being assembled with each diaphyseal component 52A, 52B, 52C, 52D, 52E. The Morse taper bores 79A, 79B, 79C, 79D, 79E, 79F of the illustrated collar components 53A, 53B, 53C, 53D, 53E, 53F are frusto-conical, with diameters of 13.87 mm (0.546 inches) at the widest points (shown at $d_5$ in FIG. 7), depths of 17.35 mm (0.683 inches), and taper angles of 2°50'0". It should be understood that these and all dimensions provided in this description are provided for illustrative purposes only; the invention is not limited to these dimensions or any other dimension unless expressly called for in one of the claims.

The Morse taper bores 79A, 79B, 79C, 79D, 79E, 79F of the collar components 53A, 53B, 53C, 53D, 53E, 53F are centered on the central longitudinal axes 81A, 81B, 81C, 81D, 81E, 81F of the collar components and in communication with longitudinal channels 83A, 83B, 83C, 83D, 83E, 83F that extend through Morse taper posts 85A, 85B, 85C, 85D, 85E, 85F. The Morse taper posts 85A, 85B, 85C, 85D, 85E, 85F of the collar components are at a first end 87A, 87B, 87C, 87D, 87E, 87F of the collar components and the Morse taper bores 79A, 79B, 79C, 79D, 79E, 79F of the collar components are at a second end 89A, 89B, 89C, 89D, 89E, 89F of the collar components.

Figure 8:
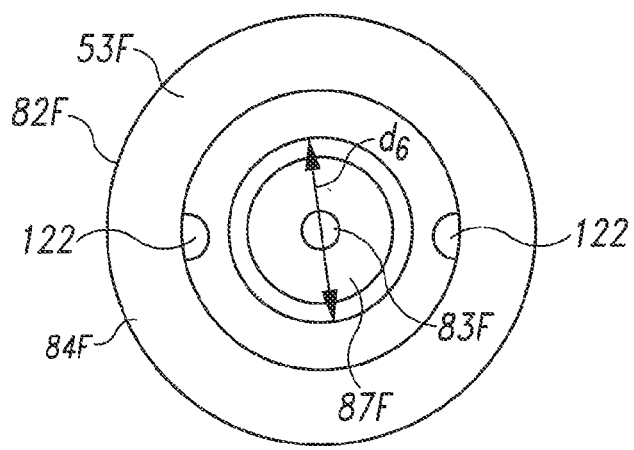
FIG. 8 is a view of the opposite end of the collar component of FIG. 7.

The Morse taper posts 85A, 85B, 85C, 85D, 85E, 85F of the collar components 53A, 53B, 53C, 53D, 53E, 53F are sized and shaped to be received within and frictionally lock with the Morse taper bores of the bone replacement components, that is, the articulation components and the intercalary components. Accordingly, the Morse taper posts 85A, 85B, 85C, 85D, 85E, 85F may each have a length of 20.32 mm (0.800 inches) to be received in Morse taper bores in the articulation components and intercalary components having a depth of about 24.13 mm (0.950 inches). Maximum outer diameters (shown at $d_5$ in FIG. 8) for the Morse taper posts of the collar components may be, for example, 19.01 mm (0.7485 inches), to be received in bores having maximum diameters of, for example, 19.05 mm (0.7500 inches). For all of the Morse tapers in the system, any typical angle for Morse tapers may be used, such as 2°24'35", for example. It should be understood that dimensions and angles are provided herein by way of example only; the present invention is not limited to any particular dimension or angle unless expressly called for in the claims.

In each of the illustrated sizes of collar components 53A, 53B, 53C, 53D, 53E, 53F, at least a portion of the outer surface of each collar is cylindrical in shape. As shown in FIG. 3, in the extra extra small component 52A and extra small component 52B, all or substantially all of the outer surface of the collar 39A is cylindrical in shape; in the other larger sizes 52C, 52D, 52E the collars 53C, 53D, 53E, 53F include a cylindrical portion 82C, 82D, 82E, 82F at the second end 89C, 89D, 89E, 89F and a frusto-conical portion 84C, 84D, 84E, 84F at the first end 87C, 87D, 87E, 87F. A portion or all of each collar component may be porous; for example, an annular porous strip having a height (longitudinal dimension) of 10 mm may be provided on the cylindrical portions 82A, 82B, 82C, 82D, 82E, 82F for tissue attachment and ingrowth. Variations in the type and characteristics of the porous coating may be made to encourage soft tissue ingrowth, as opposed to bone ingrowth. Moreover, features may be included on the collar to allow for attachment of soft tissue or the periosteum to the collar; for example, suture holes may be provided. Preferably, a portion of each collar component has a surface that is conducive to ingrowth of the periosteum.

Each collar component 53A, 53B, 53C, 53D, 53E, 53F includes a transverse annular surface 86A, 86B, 86C, 86D, 86E, 86F that is perpendicular to the longitudinal axis 81A, 81B, 81C, 81D, 81E, 81F of the collar component. The transverse annular surfaces 86A, 86B, 86C, 86D, 86E, 86F surround the openings into the Morse taper bores 79A, 79B, 79C, 79D, 79E, 79F and have different diameters (shown for example at $d_4$ in FIG. 7). Examples of possible longitudinal lengths of the collar components apart from the Morse taper posts (shown at 1 in FIG. 3 at component 53F) as well as possible dimensions for $d_4$ are provided in the following table:

| Component | Dimension | |
|---|---|---|
| | $d_4$ | L |
| 53A | 15 mm | 20 mm |
| 53B | 19 mm | 20 mm |
| 53C | 23 mm | 20 mm |
| 53D | 27 mm | 20 mm |
| 53E | 31 mm | 20 mm |
| 53F | 35 mm | 20 mm |

With a porous coating, the dimension $d_4$ should increase by about 1.5 mm (sixty-thousandths of an inch). It should be understood that these dimensions are provided as examples only; the present invention is not limited to any particular dimension unless expressly called for in the claims. The transverse annular surface 86A, 86B, 86C, 86D, 86E, 86F may be porous or smooth over all or a portion of its surface area. If porous, the transverse annular surface may provide a surface conducive to tissue ingrowth. It may be desirable to limit any porous coating to the outer portions of the transverse annular surface.

Figure 9:
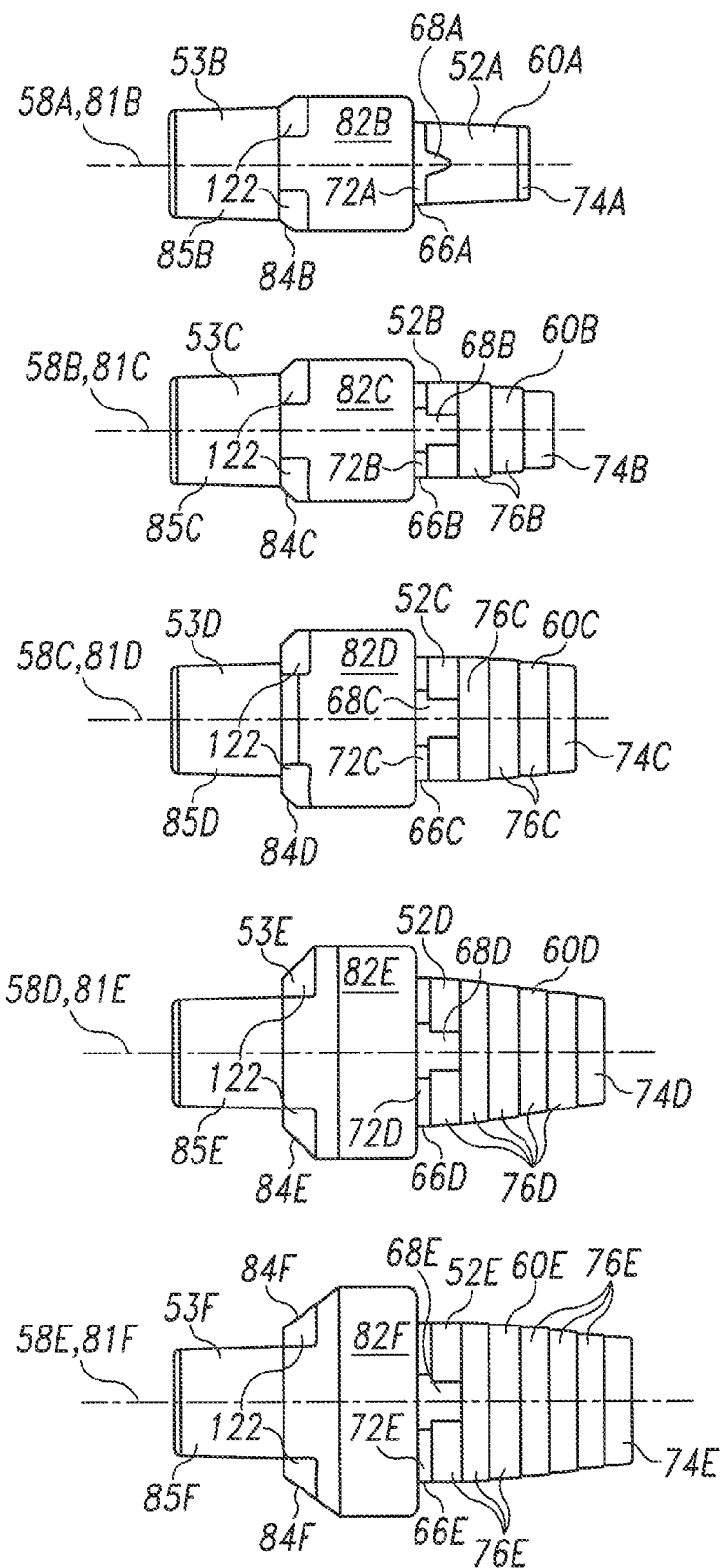
FIG. 9 is an elevation of one possible set of assemblies of diaphyseal components and collar components.
Figure 10:
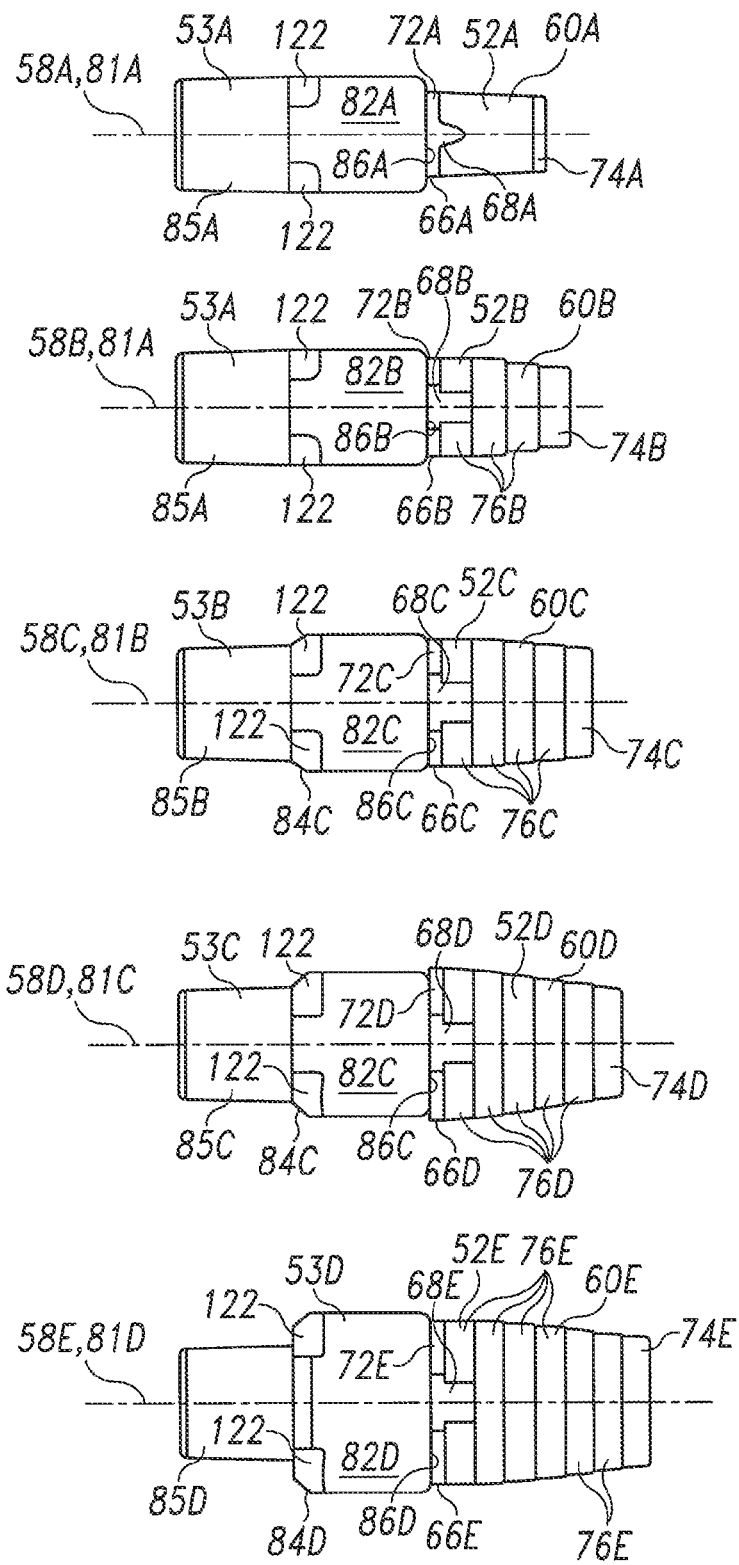
FIG. 10 is an elevation of another possible set of assemblies of diaphyseal components and collar components.

FIGS. 9 and 10 illustrate various assemblies of diaphyseal components 52A, 52B, 52C, 52D, 52E, 52F and collar components 53A, 53B, 53C, 53D, 53D, 53E, 53F. In the assemblies illustrated in FIG. 9, the diaphyseal components and collar components are selected so that a substantial portion of the annular surfaces 86B, 86C, 86D, 86E, 86F are exposed beyond the first step 72A, 72B, 72C, 72D, 72E of the diaphyseal implant component. In the assemblies illustrated in FIG. 10, the diaphyseal components and collar components are selected so that the outer diameters of the transverse annular surfaces 86A, 86B, 86C, 86D of the collar components substantially match the maximum transverse dimensions of the diaphyseal components.

Figure 15:
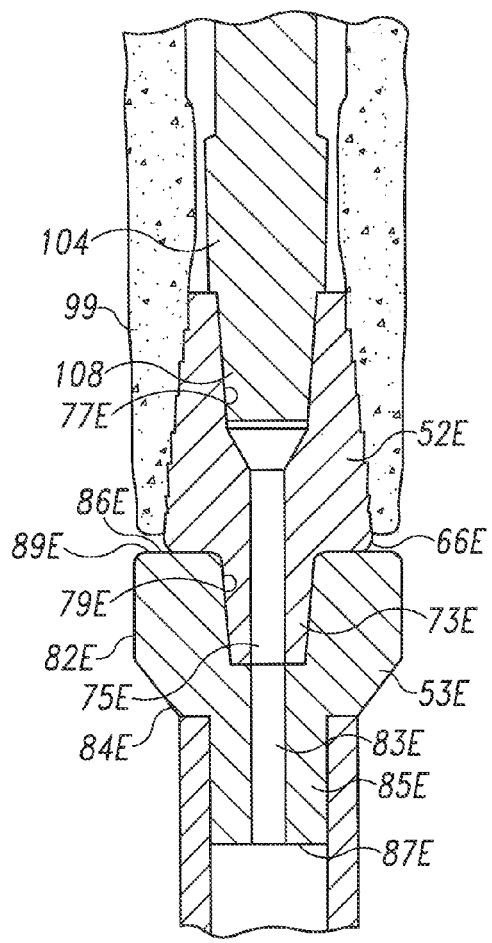
FIG. 15 is a longitudinal cross-section through a diaphyseal segment of bone and through an assembly of a stem with one of the diaphyseal components, one of the collar components and another implant component.
Figure 16:
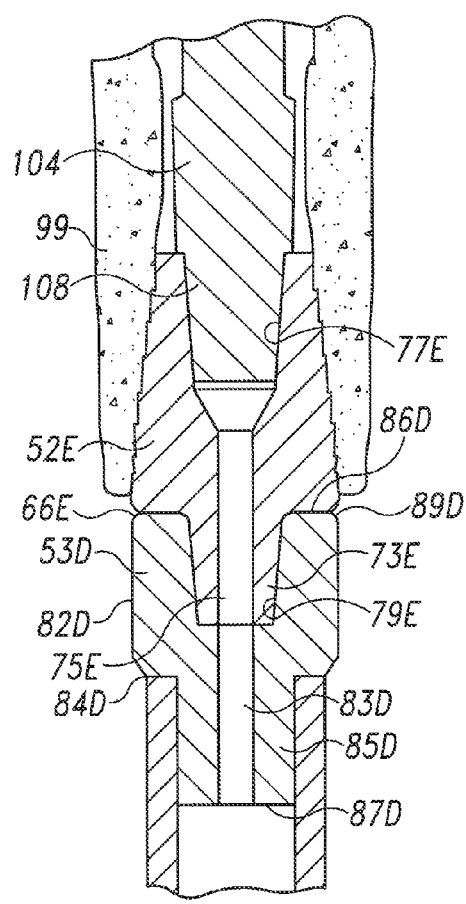
FIG. 16 is a cross-section similar to FIG. 15, but shown with the stem, diaphyseal component and other component assembled with a different collar component from the system.

FIGS. 15 and 16 illustrate the results of using assemblies of the types shown in FIGS. 9 and 10. In FIG. 15, the annular surface 86E of the collar component 53E is large enough so that the resected end of the bone 91 may bear against the outer rim of the annular surface 86E if the diaphyseal component 52E should subside in the bone. In FIG. 16, the annular surface 86D of the collar component has a smaller diameter and is substantially covered by the diaphyseal component. Depending on surgeon preference and the individual needs of the patient, with the modular system of the present invention the surgeon may opt to have the annular surface of the collar component partially exposed or substantially covered.

FIGS. 11-12 illustrate the large size diaphyseal implant component 52E and largest size of collar component 53F in exploded views with other modular implant components that may be included in a kit or system and assembled with the diaphyseal implant component 52E and collar component 53F for implantation. In FIGS. 11-12, the assembly is intended for use in replacing a portion of the distal femur. The assemblies of both FIGS. 11 and 12 include a distal femoral implant 100, a segmental implant component 102, a collar component 53F, a diaphyseal component 52E, and a stem extension. The assembly of FIG. 12 also includes an adapter component 116. Features of the adapter 116 are disclosed in more detail in U.S. patent application Ser. No. 10/817,051 entitled "Modular Implant System with Fully Porous Coated Sleeve", filed on Apr. 2, 2004 by Goodfried, Hazebrouck, Lester and Brown, the complete disclosure of which is incorporated by reference herein.

In FIG. 11, the stem extension 104 has a coronal-slotted free end or tip 106, a body 107 and a connection end 108. The connection end 108 comprises a Morse taper post in the embodiment of FIG. 8. The Morse taper post at the connection end 108 is received within and frictionally locks with the Morse taper bore 77E of the diaphyseal component 52E. In FIG. 12, the stem extension 110 has a free end or tip 112, a body 113 and a connection end 114 that comprises a male threaded member. The embodiment of FIG. 12 also includes an adapter 116 with a threaded opening (not shown) to receive the male threaded connection end 114 of the stem extension and a Morse taper post 118 to be received in the Morse taper bore 77E of the diaphyseal implant component 52E. All of the large size diaphyseal implant components 52C, 52D, 52E can be assembled with stem extensions in the manners illustrated in FIGS. 11-12. Due to constraints on the thicknesses of the walls of the tapered outer surfaces 60A, 60B of the smaller sized diaphyseal implant components 52A, 52B, accommodation is only made for connection to a stem extension with a threaded male end of the type shown in FIG. 12.

The bodies 107, 113 of the stem extensions 104, 110 may vary. For example, a substantial part of the length of the body, such as body 107 of FIG. 11, can be porous. Alternatively, the body can be sized and shaped for cemented application, like the body 113 of the stem extension 110 of FIG. 12. Alternatively, the body of the stem extension can be splined.

Figure 13:
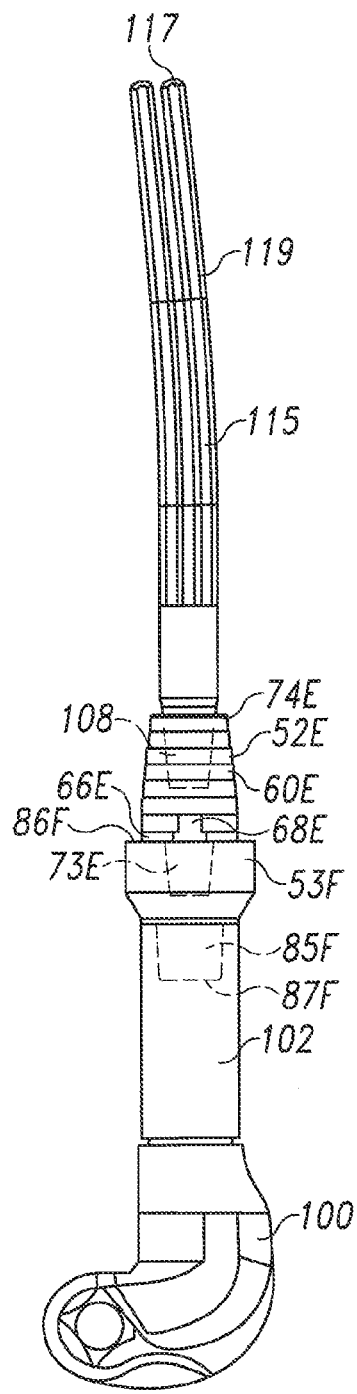
FIG. 13 is a side view of a distal femoral implant assembly including one of the diaphyseal components and collar components of FIGS. 3-4 in use with a different style of stem extension.
Figure 14:
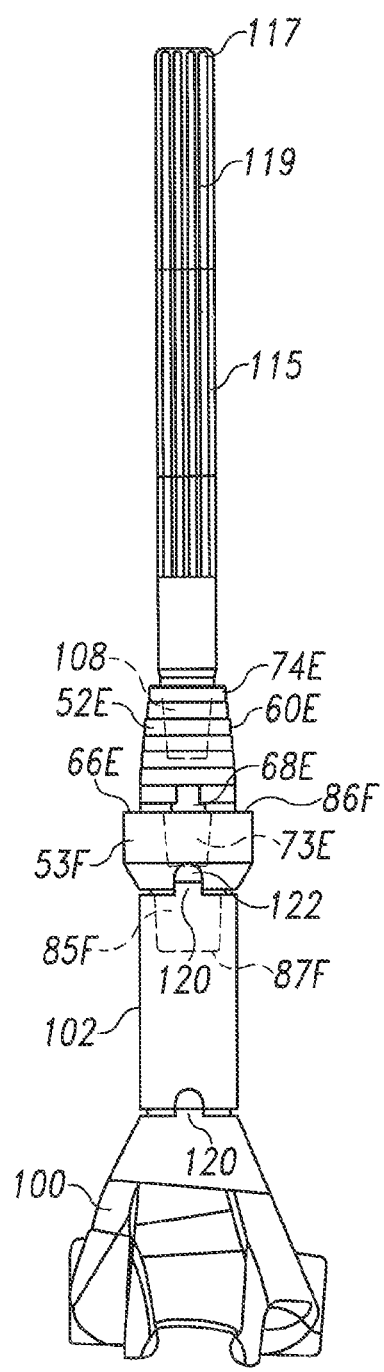
FIG. 14 is an anterior view of the distal femoral implant assembly of FIG. 13.

FIGS. 13-14 illustrate a stem extension 115 with a coronal slotted free end 117, a splined body 119, and a connection end (not shown) comprising a Morse taper post. In the embodiment of FIGS. 13-14, the splined body 119 of the stem extension 115 comprises a plurality of cutting flutes. The stem extension 115 of FIGS. 13-14 is not porous. Although in FIGS. 13-14 the free end 117 of the stem extension 115 is illustrated as being substantially flat, it may be desirable for the free end 117 to be bullet-shaped.

For the femoral articulation components 100 and segmental components 102 of FIGS. 11-14, U.S. Pat. Publication No. US2003/0204267A1, which is incorporated by reference herein in its entirety, discloses additional details regarding the Morse taper bores in the femoral and segmental components, and of appropriate Morse taper posts for use with such components.

As disclosed in U.S. Pat. Publication No. US2003/0204267A1, the distal femoral implant component 100 and segmental component 102 both include tabs 120. Each of the collar components 53A, 53B, 53C, 53D, 53E, 53F include corresponding notches 122 to receive the tabs 120 to prevent the collar components from rotating. These notches can also be used to separate the components if necessary; a tool such as that disclosed in U.S. Pat. No. 6,786,931 may be used.

It should be understood that a typical implant kit or system would include several sizes of distal femoral implant components 100, segmental components 102 and stem extensions 104, 110. It should also be understood that depending on the size and shape of the distal femoral component, it may not be necessary to use a segmental component 102; the collar components 53A, 53B, 53C, 53D, 53E, 53F could be connected directly to the femoral implant component 100.

Use of the diaphyseal components 52A, 52B, 52C, 52D, 52E and collar components 53A, 53B, 53C, 53D, 53E, 53F of the present invention is not limited to segmental components and femoral components. As illustrated in FIGS. 17-20, the diaphyseal components and collar components of the present invention can be used with other implant components having an articulation portion. For example, as shown in FIG. 17, the articulation portion of the implant component could comprise a proximal femoral component 150 (including a femoral head 152). As shown in FIG. 18 the articulation portion of the implant component could comprise a proximal tibia component 154 or other component, such as a proximal humeral component (not shown).

Figures 19, 20:
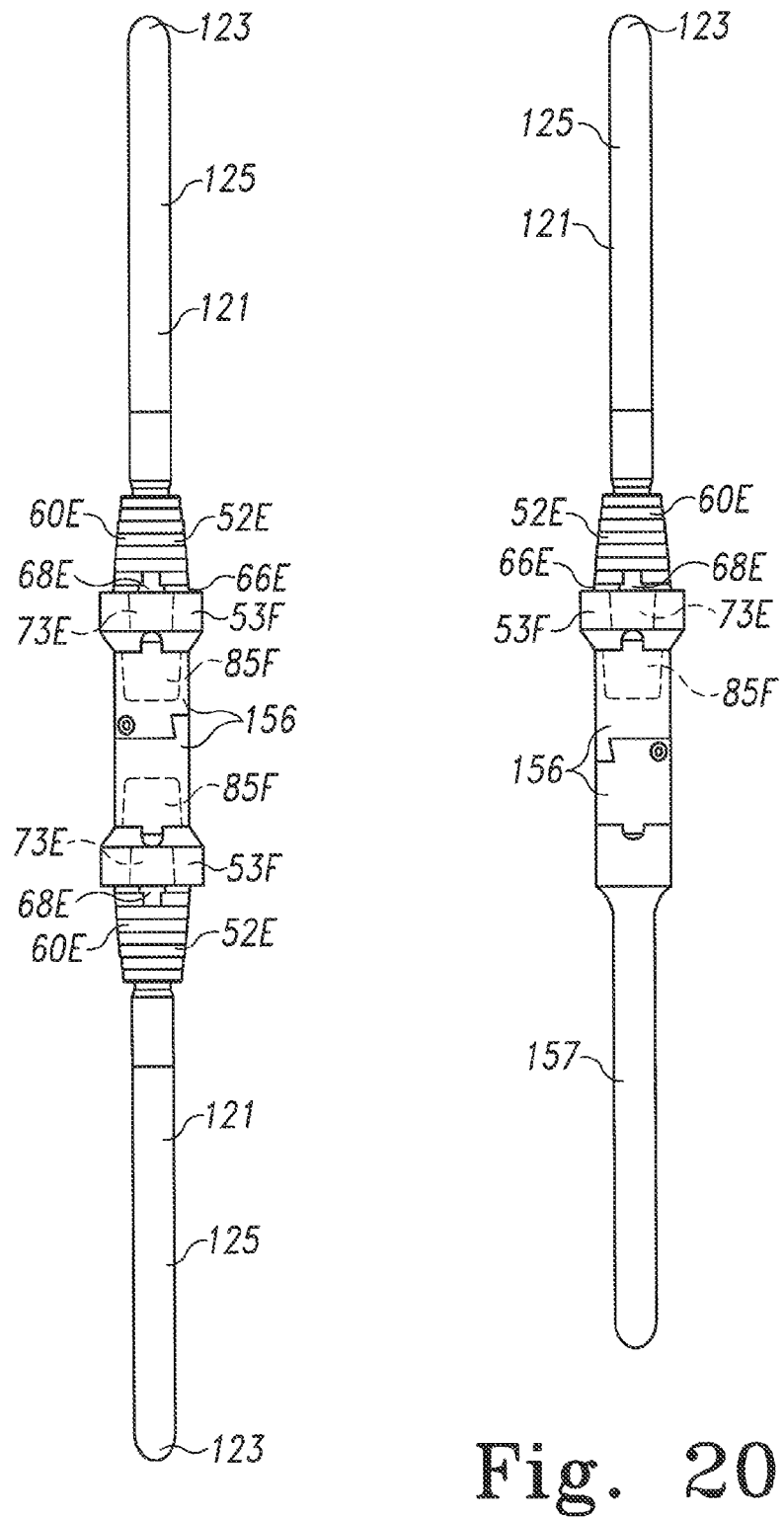
FIG. 19 is a side view of an intercalary implant assembly including two of the diaphyseal components and two of the collar components of FIGS. 3-4.
FIG. 20 is a side view of an intercalary implant assembly including one of the diaphyseal components and collar components of FIGS. 3-4.

As shown in FIGS. 19-20, the implant component could be an intercalary implant instead of an articulation component. FIG. 19 illustrates two large size diaphyseal implant components 52E and two large size collar components 53F in use with a two-piece intercalary implant 156 of the type disclosed in U.S. Publication No. US2004/0193268A1 entitled "Intercalary Prosthesis, Kit and Method," filed Mar. 31, 2003 by Hazebrouck, incorporated by reference herein in its entirety, or those disclosed in U.S. Publication No. US2004/0193267A1 entitled "Intercalary Implant," filed on Mar. 31, 2003 by Natalie Heck and Michael C. Jones (also incorporated by reference herein in its entirety). Such implants may be used with intercalary trials such as those disclosed in U.S. Publication No. US2005/0107794A1, entitled "Orthopaedic Spacer," filed on Sep. 24, 2004 by Hazebrouck, the complete disclosure of which is incorporated by reference herein. FIG. 20 illustrates a single diaphyseal component 52E and collar component 53F in use with the two-piece intercalary component 156 and a standard stem extension 157 for the LPS implant system.

In FIGS. 17-20 the stem extension is shown diagrammatically and indicated generally by reference number 121, with the free end indicated by reference number 123. Other than the bullet shape of the free end 123, no other features are shown for the body 125 of the stem extension. It should be understood that the body 125 of the stem extension 121 in any of FIGS. 17-20 could have any of the above described features, such as splined cutting flutes, a porous coating, a coronally slotted free end, or could be designed for cemented application.

All of the components of the illustrated implant systems can be made of standard materials for such implants, such as titanium and cobalt-chrome alloys.

It should be understood that although the principles of the present invention are described and illustrated with reference to implant components available from DePuy Orthopaedics, Inc., the invention is not limited to these components or their features. The principles of the present invention can be applied to other implant components, including those of other manufacturers and those subsequently developed.

Figure 21:
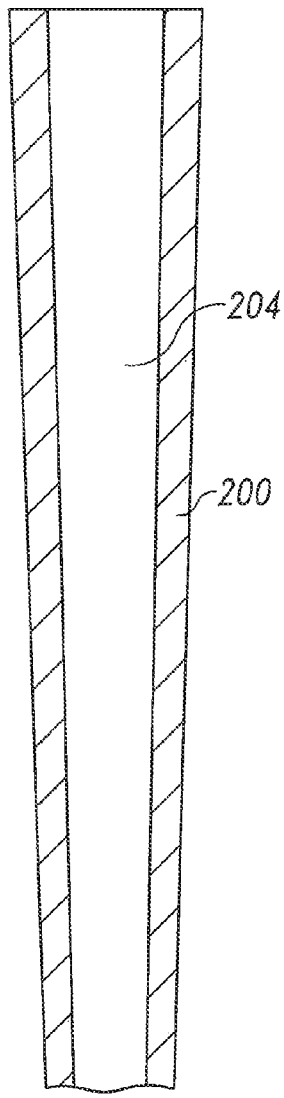
FIG. 21 is a diagrammatic cross-section of a portion of the remaining portion of the diaphysis after a portion of the femur or long bone has been resected.
Figure 22:
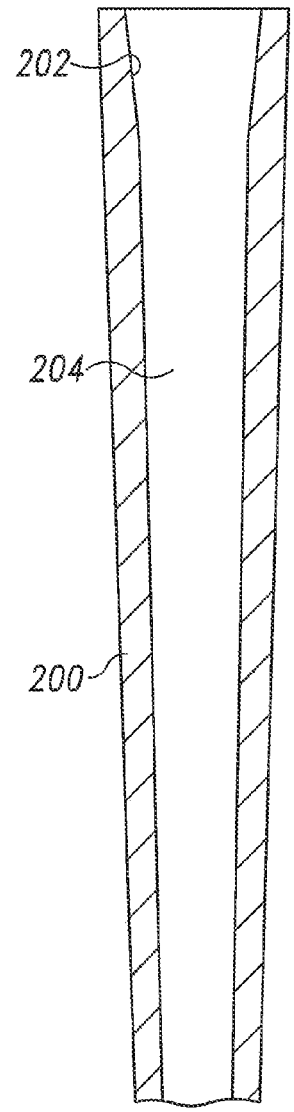
FIG. 22 illustrates the remaining resected diaphysis of FIG. 21 after a tapered bore has been prepared at the resection site of the bone.
Figure 23:
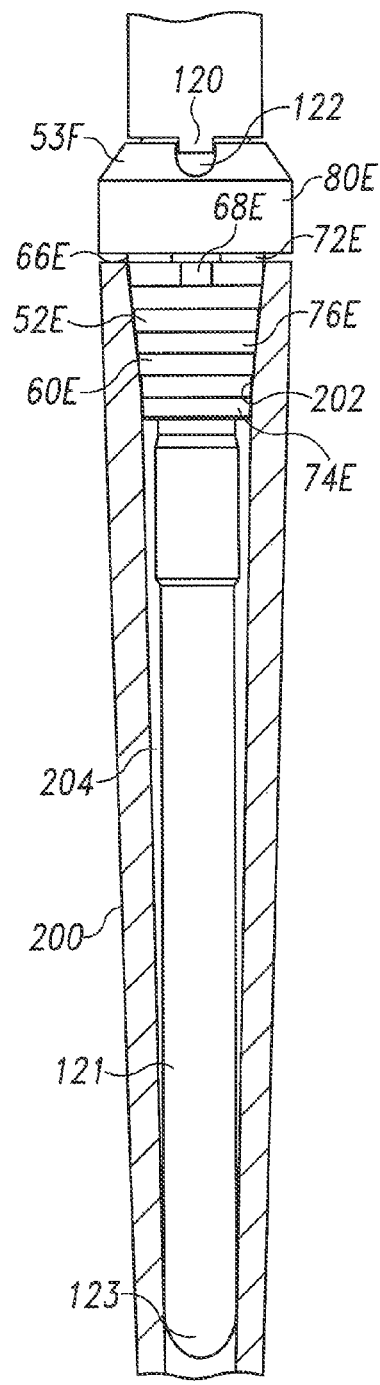
FIG. 23 illustrates the remaining resected diaphysis of FIG. 22 with an implant assembly including a diaphyseal component fully seated in the bone and a collar component outside of the bone.

In use, depending on the condition of the native bone tissue, the orthopaedic surgeon will determine the amount of bone to be resected from the femur (or other long bone). Commercially available instrumentation can be used to resect the bone in the appropriate manner. The diaphysis of a resected bone is illustrated in FIGS. 21-23 at 200. If it is desirable to use a diaphyseal implant component 52A, 52B, 52C, 52D, 52E to secure the implant in place, the surgeon can then select an appropriate size of diaphyseal implant component 52A, 52B, 52C, 52D or 52E for the individual patient. The diaphysis 200 of the bone can then be prepared to receive the selected diaphyseal implant component 52A, 52B, 52C, 52D or 52E. The surgeon can use a conical reamer (not shown) of a size and shape matching the size and shape of the selected diaphyseal component to mill or machine the diaphysis 200 of the bone to create a tapered bore that closely matches the size and shape of the tapered outer surface 60A, 60B, 60C, 60D, 60E of the selected diaphyseal implant component. A tapered bore is illustrated in FIGS. 22-23 at 202. Since the tapered bore is created to match the size and shape of the selected diaphyseal component, the implants and techniques of the present invention are adaptable to different patient anatomies.

The surgeon may select an appropriate size collar component according to the surgeon's preferences and the needs of the patient. If the surgeon decides that the optimum patient outcome would result from the use of an assembly that provides a transverse surface to bear against the resected bone, the surgeon would select a collar component wherein the diameter of the transverse annular surface 86 is greater than the maximum transverse outer dimension of the diaphyseal component. It the surgeon decides that the optimum patient outcome would result from use of an assembly that does not provide a transverse surface to bear against the resected bone, the surgeon would select a collar component wherein the diameter of the transverse annular surface 86 does not exceed the maximum transverse outer dimension of the diaphyseal component. Once the appropriate diaphyseal and collar components are selected, the two components may be frictionally locked together by pushing the Morse taper post 73A, 73B, 73C, 73D, 73E of the diaphyseal component into the mating Morse taper bore 79B, 79C, 79D, 79E, 79F of the collar component 53A, 53B, 53C, 53D, 53E, 53F.

The surgeon may select a stem extension appropriate to the individual patient and assemble the stem extension with the subassembly of the diaphyseal component and the collar component. The surgeon would also assemble the intercalary component or articulation component with the other parts by inserting the Morse taper post of the collar component into the mating Morse taper bore of the intercalary or articulation component. The stem extension and part of the diaphyseal implant component of the assembled implant, can then be inserted into the bone as illustrated in FIG. 23 and positioned with the tip or free end of the stem extension engaging the bone surface of the intramedullary canal 204 and with the tapered outer surface 60A, 60B, 60C, 60D or 60E bearing against the tapered diaphyseal bone defining the tapered bore 202. The stem extension in FIG. 21 is identified with reference number 121 and its free end is identified with reference number 123; as discussed above with respect to FIGS. 17-20, the stem extension 121 is illustrated diagrammatically, and can include any of the features of the stem extensions 104, 110, 115 described above. Because of the shapes and textures of the implant components 121, 52A, 52B, 52C, 52D or 52E received within the bone, there should be no binding before the diaphyseal component 52A, 52B, 52C, 52D or 52E is fully seated. Accordingly, implantation should be relatively easy.

It should be understood that the present invention is not limited to any particular order of assembly of the components. For example, the collar component and articulation component could be assembled and then assembled with the diaphyseal component, or the collar component and diaphyseal component can be assembled and then assembled with the articulation component.

Generally, when implanted, the first step 72A, 72B, 72C, 72D, 72E of each of the diaphyseal implant components 52A, 52B, 52C, 52D, 52E and the outer surface of the collar component (other than the Morse taper post) will be exposed outside of the bone as shown in FIG. 23. Subsequently, some subsidence of the implant can occur over time without damage to the bone. The flats 68E prevent the diaphyseal component 52E from rotating or turning in the tapered bore 202 that the surgeon created for it.

As shown in FIG. 23, when fully seated, the implant assembly contacts the bone at both the tip 123 of the stem extension 121 and at the tapered outer surface 60E of the diaphyseal component 52E. Bone ingrowth can occur around the entire tapered outer surface 60E of the diaphyseal implant component 52E. Depending on the intramedullary canal anatomy and characteristics of the stem extension, bone ingrowth can also occur along all or part of the body of the stem; for example, bone ingrowth could occur at the free end of the stem extension and/or at any area between the diaphyseal component and the free end of the stem. For example, if a cemented stem extension is used, such as the stem extension 110 of FIG. 12, there should be no bone ingrowth along the body of the stem. Similarly, no substantial bone ingrowth should occur along the stem with the splined stem extension 115 of FIGS. 13-14. If all or part of the stem extension 104 of FIG. 11 is porous, bone ingrowth can be expected at the porous area.

With the stepped designs of the larger diaphyseal implant components, such as diaphyseal implant components 52B, 52C, 52D, 52E, shear forces are essentially converted to compressive loads, and the compressive loads are spread among the steps 74, 76 contacting the diaphyseal bone defining the tapered bore 202. Accordingly, the implant is immediately stable and capable of bearing weight. In addition, with the bone bearing the axial load at the tapered bore 202, there is no disadvantageous stress shielding of the bone. Moreover, with the implant assembly contacting the bone at both the tip 106 of the stem extension and at the contacting surfaces of the diaphyseal bone defining the tapered bore 202 and tapered outer surface 60, any moment arm is significantly reduced if not eliminated. With bone ingrowth occurring at both spaced locations over time, long term implant stability should be improved. Accordingly, the implant assembly of the present invention should be less likely to loosen over time.

As can be seen in FIGS. 15 and 23, a small gap 220 may be between the exposed resected bone surface and the transverse annular surface 86E of the collar 53E when implanted. If the implant does subside, this gap can decrease to the point that the transverse annular surface 86E bears directly against the exposed resected bone surface. If the transverse annular surface is porous, tissue ingrowth can occur in the gap 220 over time to seal the intramedullary canal 204 against debris.

With any of the illustrated assemblies, the periosteum of the bone should grow into the porous outer surface of the collar component 53. Essentially the ingrowth of tissue along the cylindrical outer surface of the collar (or along the exposed portion of the transverse annular surface of the collar) should effectively seal off the intramedullary canal, to thereby protect the patient from injury or disease resulting from debris entering into the intramedullary canal.

With the modular implant system of the present invention, it should be possible to reduce inventory of the necessary parts in an implant system or kit.

It should also be understood that a typical surgical kit would also include trial implant components like those shown in FIGS. 3-4 and 8-15. The surgeon would typically assemble a trial implant and temporarily secure the trial implant assembly in place on the prepared diaphyseal bone to ensure that the assembled implant will be the optimum for the individual patient's needs. The trial components can have features like those described above for the final implant components.

In case it is necessary to ultimately remove the implant assembly from the patient, such removal should not require the removal of excessive bone stock, since it should only be necessary to remove the portion of the diaphysis defining the tapered bore 202.

Various modifications and additions can be made to the above-described embodiments without departing from spirit of the invention. All such modifications and additions are intended to fall within the scope of the claims unless the claims expressly call for a specific construction.

We claim:

1. A modular orthopaedic implant system comprising:
a diaphyseal component and a collar component,
the diaphyseal component including:
   a first end having a post;
   a second end spaced from the post and having a bore co-axial with the post of the first end;
   a longitudinal axis extending from the first end to the second end, the longitudinal axis extending through the post at the first end and the bore at the second end;
   a tapered outer surface between the post and the second end, the tapered outer surface having a maximum outer transverse dimension at the junction with the post and a minimum outer transverse dimension at the second end, wherein at least part of the tapered outer surface is porous, and wherein the maximum outer transverse dimension of the tapered surface defines a maximum transverse dimension of the diaphyseal component, the minimum outer transverse dimension of the tapered outer surface and the maximum outer transverse dimensions of the tapered outer surface and the diaphyseal component being perpendicular to the longitudinal axis of the diaphyseal component;
the collar component including:
   a first end having a post;
   a second end having a bore co-axial with the post of the first end;
   a longitudinal axis extending from the first end to the second end, the longitudinal axis extending through the post at the first end and the bore at the second end;
   a substantially cylindrical portion between the first end and second end and surrounding at least a portion of the bore at the second end, the substantially cylindrical portion including an annular surface disposed perpendicular to the longitudinal axis of the collar component at the second end of the collar component, the annular surface having a maximum outer transverse dimension, the substantially cylindrical portion having a maximum outer transverse dimension, the maximum outer transverse dimension of the annular surface being the same as the maximum outer tranverse dimension of the cylindrical portion of the collar and greater than the maximum outer tranverse dimension of the tapered outer surface of the diaphyseal component, the annular surface of the collar having the same maximum outer transverse dimension along two perpendicular axes, the maximum outer transverse dimensions of the substantially cylindrical portion and annular surface being perpendicular to the longitudinal axis of the collar component;
wherein the post of the diaphyseal component and the bore of the collar component have complementary sizes and shapes so that the diaphyseal component and the collar component can be assembled and locked together by inserting the post of the diaphyseal component into the bore of the collar component.

2. The orthopaedic implant system of claim 1 wherein:
the post of the diaphyseal component has a frusto-conical shape and a maximum outer diameter and the post of the collar component has a frusto-conical shape and a maximum outer diameter; and
the maximum outer diameter of the post of the collar component is greater than the maximum outer diameter of the post of the diaphyseal component.

3. The orthopaedic implant system of claim 2 wherein:
the post of the diaphyseal component comprises a Morse taper post and the bore of the collar component comprises a Morse taper bore; and
the Morse taper post and Morse taper bore are sized and shaped to frictionally lock when assembled.

4. The orthopaedic implant system of claim 1 wherein the tapered outer surface of the diaphyseal component has the same maximum outer transverse dimension along two perpendicular transverse axes.

5. The orthopaedic implant system of claim 1 wherein the tapered outer surface of the diaphyseal component includes a first step adjacent to the post, a last step and an intermediate step between the first step and the last step, each step having a maximum outer transverse dimension and a longitudinal height, the maximum outer transverse dimension of the tapered outer surface being at the first step and the minimum outer transverse dimension of the tapered outer surface being at the last step.

6. The orthopaedic implant system of claim 5 wherein the longitudinal height of the first step is less than the longitudinal height of the last step and less than the longitudinal height of the intermediate step.

7. The orthopaedic implant system of claim 1 further comprising a plurality of diaphyseal components of different size.

8. The orthopaedic implant system of claim 1 further comprising a plurality of collar components of different size.

9. The orthopaedic implant system of claim 1 further comprising a stem for attachment to the second end of the diaphyseal component.

10. The orthopaedic implant system of claim 9 further comprising another implant component having a different shape than the stem, diaphyseal component and collar component for attachment to the post of the collar component, wherein the other implant component is selected from the group consisting of articulation components and intercalary components.

11. The modular orthopaedic implant system of claim 1 further comprising a second collar component, the second collar component including:
a first end having a post;
a second end having a bore co-axial with the post of the first end;
a longitudinal axis extending from the first end to the second end, the longitudinal axis extending through the post at the first end and the bore at the second end;
a substantially cylindrical portion between the first end and second end and surrounding at least a portion of the bore at the second end, the substantially cylindrical portion including an annular surface disposed perpendicular to the longitudinal axis of the collar component at the second end of the collar component, the annular surface having a maximum outer transverse dimension perpendicular to the longitudinal axis of the second collar component;
wherein the post of the diaphyseal component and the bore of the second collar component have complementary sizes and shapes so that the diaphyseal component and the second collar component can be assembled and locked together by inserting the post of the diaphyseal component into the bore of the second collar component; and
wherein the maximum outer transverse dimension of the annular surface of the first collar component is greater than the maximum outer transverse dimension and the annular surface of the second collar component.

12. The orthopaedic implant system of claim 11 wherein the maximum outer transverse dimension of the tapered outer surface of the diaphyseal component is greater than the maximum outer transverse dimension of the annular surface of the first collar component and is not greater than the maximum outer transverse dimension of the annular surface of the second collar component.

13. The orthopaedic implant system of claim 1 further comprising a second diaphyseal component including:
a first end having a post;
a second end having a bore co-axial with the post at the first end;
a longitudinal axis extending from the first end to the second end, the longitudinal axis extending through the post at the first end and the bore at the second end; and
a tapered outer surface between the post and the second end, the tapered outer surface having a maximum outer transverse dimension at the junction with the post and a minimum outer transverse dimension at the second end, the maximum outer transverse dimension and minimum outer transverse dimension of the second diaphyseal component being perpendicular to the longitudinal axis of the second diaphyseal component, wherein at least part of the tapered outer surface is porous;
wherein the maximum outer transverse dimension of the tapered outer surface of the second diaphyseal component is greater than the maximum outer transverse dimension of the tapered outer surface of the first diaphyseal component; and
wherein the post of the second diaphyseal component and the bore of the collar component have complementary sizes and shapes so that the second diaphyseal component and the collar component can be assembled and locked together by inserting the post of the second diaphyseal component in the bore of the collar component.

14. The orthopaedic implant system of claim 1 wherein the collar component includes a frusto-conical portion between the substantially cylindrical portion and the post, the frusto-conical portion tapering from a maximum outer transverse dimension at the junction with substantially cylindrical portion, the fruso-conical portion and the post of the collar component having different shapes.

15. An orthopaedic implant system for replacing a portion of a long bone, the long bone having an articulation portion, a diaphysis and an intramedullary canal, the kit including:
a plurality of articulation components, each articulation component being shaped and sized to replace the articulation portion of the long bone, each modular articulation component including a tapered bore having a first size;
a plurality of modular stems to be received in the intramedullary canal of the long bone, each stem having a free end and an opposite end capable of being connected to another implant component;
a plurality of modular diaphyseal implant components capable of being connected to the modular stems and a plurality of modular collar components,
wherein:
each diaphyseal implant component includes:
a first end having a tapered post;
a second end for connection to a selected modular stem;
a longitudinal axis extending between the first end and the second end;
a tapered outer surface extending from the tapered post to the second end, the tapered outer surface having a first step adjacent to the post, a last step at the second end and an intermediate step between the first step and the last step, each step having a maximum outer transverse dimension and a longitudinal height, the maximum outer transverse dimension of the tapered outer surface being at the first step and the minimum outer transverse dimension of the tapered surface being at the last step;
each collar component includes:
a first end having a tapered post;
a second end having a tapered bore co-axial with the post of the first end, the tapered bore of the collar component being smaller than the tapered bore of the articulation component;
a longitudinal axis extending from the first end to the second end, the longitudinal axis extending through the post at the first end and the bore on the second end;
a substantially cylindrical portion between the first end and the second end and surrounding at least a portion of the bore at the second end, the substantially cylindrical portion including an annular surface disposed transverse to the longitudinal axis of the collar component, the substantially cylindrical portion and annular surface of each collar component defining a maximum outer transverse dimension of that collar component;

a frusto-conical portion between the substantially cylindrical portion and the post of the collar component, the frusto-conical portion tapering from a maximum transverse dimension at the junction with the substantially cylindrical portion, the frusto-conical portion and the tapered post of the collar component having different shapes;

wherein the tapered post of each collar component is sized and shaped so that each collar component can be assembled with each articulation component and frictionally locked together by inserting the tapered post of the collar into the tapered bore of the articulation component;

wherein the maximum outer transverse dimension of one collar component is greater than the maximum outer transverse dimension of another collar component; and wherein the tapered post of each diaphyseal component is sized and shaped so that each diaphyseal component can be assembled with each collar component and frictionally locked together by inserting the tapered post of the diaphyseal component into the tapered bore of the collar component.

16. The orthopaedic implant system of claim 15 wherein the tapered post of each diaphyseal component has a smaller maximum outer diameter than the tapered post of each collar component.

17. The orthopaedic implant system of claim 15 wherein the maximum outer transverse dimension of the cylindrical portion of one collar component is greater than the maximum outer transverse dimension of the cylindrical portion of another collar component.

18. The orthopaedic implant system of claim 15 wherein at least one of the diaphyseal components has the same maximum outer transverse dimension along two perpendicular transverse axes.

19. The orthopaedic implant system of claim 18 wherein another of the diaphyseal components has the same maximum outer transverse dimension along two perpendicular transverse axes.

20. The orthopaedic implant system of claim 15 wherein the longitudinal height of the first step of at least one of the diaphyseal components is less than the longitudinal height of the last step and less than the longitudinal height of the intermediate step of that diaphyseal component.

21. The orthopaedic implant system of claim 15 further comprising a plurality of intercalary implant components shaped to replace a segment of the diaphysis of the long bone.

22. The orthopaedic implant system of claim 15 wherein:
the plurality of modular diaphyseal implant components comprises a plurality of sizes of diaphyseal implant components, each size of diaphyseal implant components having a different maximum outer transverse dimension; and the maximum outer transverse dimension of at least one of the modular collar components is greater than the maximum outer transverse dimension of the largest diaphyseal implant component.

* * * * *